United States Patent [19]

Foster

[11] Patent Number: 4,537,192

[45] Date of Patent: Aug. 27, 1985

[54] UNITARY ENDOTRACHEAL TUBE HOLDER

[76] Inventor: Billy R. Foster, 1040 Glenn Common, Livermore, Calif. 94550

[21] Appl. No.: 388,210

[22] Filed: Jun. 14, 1982

Related U.S. Application Data

[63] Continuation of Ser. No. 167,419, Jul. 11, 1980, Pat. No. 4,331,143.

[51] Int. Cl.³ .............................................. A61M 25/00
[52] U.S. Cl. ........................... 128/207.17; 128/207.14; 128/DIG. 26
[58] Field of Search ...................... 128/207.17, 207.14, 128/207.15, 200.26, 207.13, 206.18, 206.12, 206.19, 206.28, 206.29, 207.11, DIG. 26

[56] References Cited

U.S. PATENT DOCUMENTS

| | | | |
|---|---|---|---|
| 1,101,756 | 6/1914 | Nesvadba | 128/206.19 |
| 1,579,449 | 4/1926 | Hubbell | 128/206.12 |
| 2,905,173 | 9/1959 | Wold | 128/207.11 |
| 3,046,989 | 7/1962 | Hill | 128/207.18 |
| 4,191,180 | 5/1980 | Colley et al. | 128/207.17 |
| 4,328,797 | 5/1982 | Rollins, III et al. | 128/205.25 |
| 4,331,143 | 5/1982 | Foster | 128/207.17 |
| 4,354,488 | 10/1982 | Bartos | 128/207.13 |

FOREIGN PATENT DOCUMENTS 503739  6/1964  Canada ........................... 128/207.18

OTHER PUBLICATIONS

Publications of the American National Standards Institute: ANSI Z79.1-1974; ANSI Z79.3-1983.

Primary Examiner—Henry J. Recla
Attorney, Agent, or Firm—Francis H. Lewis

[57] ABSTRACT

An endotracheal tube holder includes a thin contoured plate fitting over the patient's nose, held in place by an elastic strap attached to either side of the plate and extending around the back of the patient's head. A pair of supplemental elastic straps are attached to the member, the opposite ends being fastened adjustably and slidably along the first strap on opposite sides of the patient's face. The opposite ends of the supplemental straps are attached to the lower portion of the support member, and provide stability in holding said member on the patient's face. A notched opening is located at the lower edge of the support member, into which an endotracheal tube may be laterally inserted and frictionally held in place. The straps may be adjusted or tightened by pulling on the ends.

9 Claims, 1 Drawing Figure

UNITARY ENDOTRACHEAL TUBE HOLDER

CROSS REFERENCES

This is a continuation of Ser. No. 167,419 filed July 11, 1980, now U.S. Pat. No. 4,331,143.

BACKGROUND OF THE INVENTION

1. Field of the Invention

This invention pertains generally to the field of medical and surgical devices, and more particularly to the field of devices for holding or supporting endotracheal tubes during medical treatment or surgery.

2. Description of the Prior Art

During medical treatment or surgery it is often necessary to provide an unobstructed passage or airway to the patient's lungs to administer oxygen or to facilitate breathing. This problem arises especially during acute situations involving blockage of the mouth, throat or tracheal passage by blood, mucus, or other foreign material. The problem is solved by insertion of an endotracheal tube through the patient's mouth and into the trachea to provide a free flow of air or oxygen. This tube must be maintained in its proper position for extended periods of time. It is desirable to provide means other than manual for holding this tube in place so that the surgeon's or technician's hands are free for other activities during treatment.

A common and typical method for maintaining the position of the endotracheal tube is by means of adhesive tape placed over the patient's mouth and wrapped around the tube. This traditional method is inconvenient and time consuming, and suffers from several drawbacks. Generally a considerable amount of tape is required, and in medical emergency situations valuable time must be spent taping the tube in place. Once the tube has been secured by this method it will remain in place only temporarily, because sweat, saliva, blood, or other secretions are absorbed by the adhesive tape, causing it to loosen and allowing the tube to become displaced. Therefore the tape must be removed periodically and fresh tape must be applied. Even when fresh adhesive tape is used, considerable skill is required to wrap the tape in such a manner as to hold the tube immobile because of the inherent flexibility of the tape. Further, the adhesive tape obstructs the patient's mouth so that blood or other foreign fluids cannot be removed by a suction tube while the endotracheal tube is in place, unless the suction tube is also rendered immobile by the tape and both tubes are installed simultaneously. Finally, this use of adhesive tape causes considerable discomfort to the patient.

Several devices have been developed in the past to attempt to overcome some of these and other drawbacks of the adhesive tape method for supporting endotracheal tubes. One typical device is disclosed in U.S. Pat. No. 3,774,616 (White, et al.) which teaches an endotracheal tube holder fastened to a face plate, bite block and airway fitting into and over the patient's mouth. The entire configuration is held in place by an adjustable strap passing around the patient's upper neck. This use of a bite block has several disadvantages, in that tearing of gum tissue and trauma to the interior of the patient's mouth may be caused. The bite block and airway must be inserted over the patient's tongue; however, the face plate restricts the access of a tongue depressor to the corners of the patient's mouth, and hinders this insertion. Also, the position of the strap around the patient's neck is such that it can be dislocated and the tube holder may be dislodged by involuntary motion or spasms of the patient's head.

A similar face-plate device without the bite block and airway is disclosed in U.S. Pat. No. 3,924,636 (Addison). This device and the White device share the disadvantage that access to the patient's mouth is restricted by the face plate. Both devices are unsuitable for medical emergency room applications for this reason. In addition, this device employs a plastery adhesive to fasten the face plate over the patient's mouth, and thus it encounters many of the problems associated with the use of adhesive tape.

U.S. Pat. No. 3,946,742 (Eross) discloses an endotracheal tube holder having a short C-shaped bite member and tube retainer, movably fastened by an arm to an adjustable strap passing around the patient's chin and the back of the upper neck. The tube retainer arm rests against the patient's chin, generally causing discomfort and trauma. Accordingly, the position of the arm must be changed periodically. This device has been found unsatisfactory in many instances because it does not hold the tube firmly in place but allows it to shift position in all directions in the patient's mouth. The commercially available version of this device is provided with an additional stabilizing chin strap (not disclosed in the above patent), but this chin strap is unsuitable for patients with dentures. Further, this device is awkward and difficult to adjust and fasten quickly to an emergency room patient who is moving involuntarily.

Another tube-holding device is disclosed in U.S. Pat. No. 4,114,626 issued to Beran. This patent describes a device for fastening a tube into the nose or mouth of a patient by means of a pressure-sensitive adhesive material. This device suffers from many of the drawbacks associated with the use of adhesive tape or plastery adhesives discussed above. In particular, it lacks the mechanical stability necessary to hold a tube firmly in a fixed position in the patient's mouth. It further results in discomfort to the patient, arising from the use of adhesive patches on the skin.

U.S. Pat. No. 2,831,487 (Tafilaw) discloses a catheter device having a noseplate fitting over the nose of a patient, held in place by an elastic strap around the patient's head. This plate supports and serves as a guide for tubes inserted into the patient's nostrils. These tubes are held in place by channels along the inner surface of the nose plate, and accordingly the tubes must be bent into a hairpin shape at the point directly below the nostrils. Although this device provides an improved method for holding nasal catheters in place, it is unsuitable for endotracheal tubes which are generally larger in diameter, and cannot be subjected to a hairpin bend without collapsing. Accordingly, the concept taught by Tafilaw in unsatisfactory when applied to these endotracheal tubes. In addition, the nose plate in Tafilaw covers the entire nose including the nostrils, and tends to inhibit access to the nostrils which would be desirable during the use of an endotracheal tube.

Yet another tube-holding device is disclosed in U.S. Pat. No. 3,972,321 (Proctor) which teaches a tube-holding fixture fastened by a pair of elastic straps around the back of the patient's head. This device allows the tube to vary in its directional orientation, and does not provide means for holding the tube in a fixed direction into the patient's mouth. Accordingly, it encounters the drawbacks similar to those found in the devices of Eross, Addison, and Beran, described above.

SUMMARY OF THE INVENTION

The improved endotracheal tube holder disclosed herein provides a rigid support member shaped over the patient's nose, leaving sufficient access to the patient's nostrils if necessary. The member is a heart shaped vertically curved plate extending across the ridge of the patient's nose, and downward over the patient's upper lip, with a notch provided in the lower section for holding in place an endotracheal tube. The tube may be snapped laterally in place into the notch in the support member. The plate is held in place over the patient's nose by an elastic strap extending around the back of the head with the ends adjustably attached to the wings of the plate in its upper portion. A second pair of elastic stabilizing straps are attached to the underside of the plate at a point directly above the tube-holding notch. The opposite ends of these straps are fastened to the first elastic strap at points along the sides of the patient's head near the cheeks in an adjustable manner, so that these stabilizing straps may be adjusted independently. This adjustment is achieved by sliding the fastenings of the stabilizing straps along the first supporting strap, and by further adjusting the tension in the supporting strap at its junctures with the nose plate.

It is an object of this invention to provide an endotracheal tube holder which will maintain the tube firmly and stably in its proper position while the patient's head and jaw undergo rapid or spasmodic motions, without any readjustment or re-positioning of the tube holder being necessary.

A second object of this invention is to provide an endotracheal tube holder which allows maximum access to the patient's mouth while the tube in in place.

Another object of this invention is to provide an endotracheal tube holder which may be rapidly and easily applied to the patient without requiring any substantial adjustments.

Another object of this invention is to provide an endotracheal tube holder which will not cause any unnecessary injury or trauma to the patient's mouth, or other discomfort to the patient.

A further object of this invention is to provide an endotracheal tube holder which will maintain its position for extended periods of time, without any necessity for re-positioning or readjustment.

These and other objects, advantages, characteristics and features of this invention may be better understood by examining the following drawings together with the detailed description.

DETAILED DESCRIPTION OF THE PREFERRED EMBODIMENT

Figure 1:
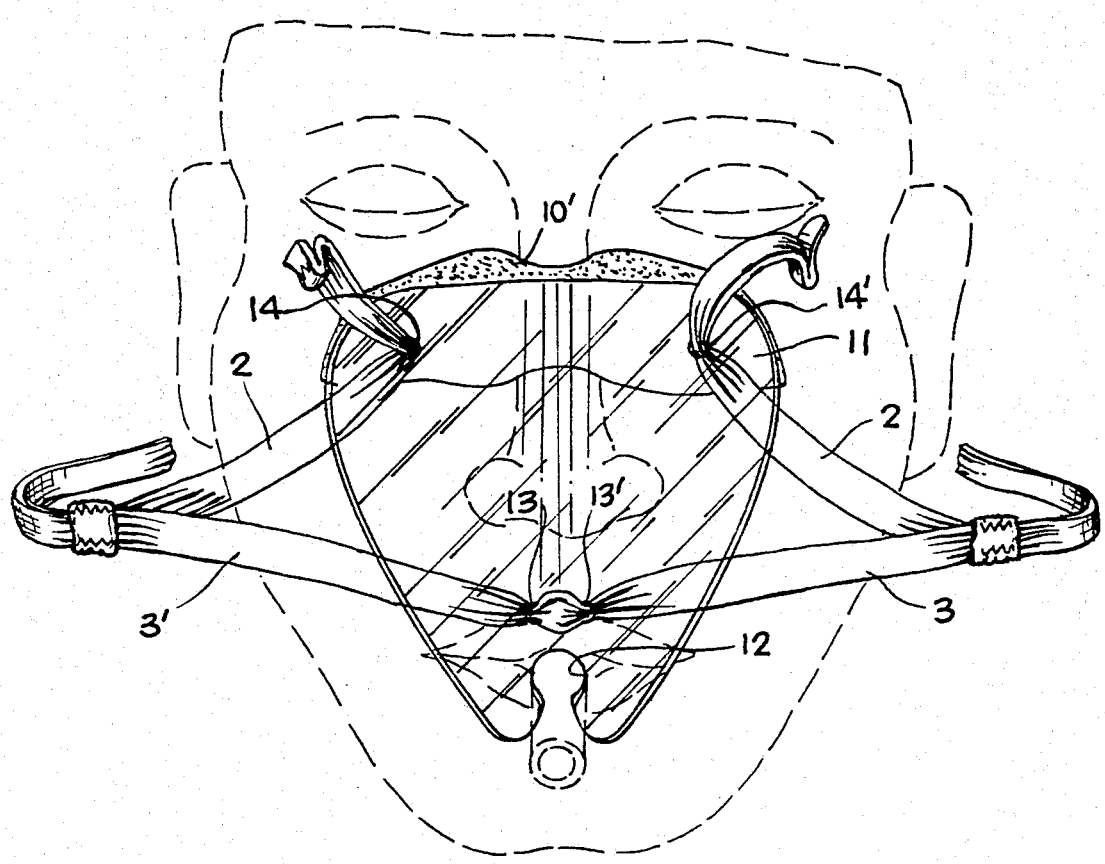
FIG. 1 is a front elevational view of the tube holder shown in position for use on a patient.

Referring to the drawing, the plate member 11 is shaped to fit over the patient's nose and extends downward over the mouth. The lower edge of the plate is provided with an upwardly extending indentation 12, forming a partially circular hole in the plate with a removed section below this circular orifice which is narrower than its diameter, as shown the figure. This indentation configuration allows an endotracheal tube to be pressed laterally and upwardly through the removed section into the circular orifice, which grips the tube and holds it in place during service. Located immediately above the indentation are holes 13, 13' in the plate member 11, through which the elastic straps 3, 3' are threaded and attached to the plate member 11. The opposite ends of the straps 3, 3' are frictionally and adjustably attached to the straps 2 to permit adjustment of the tension in straps 3, 3'. Similar holes 14, 14' are located in the plate 11 near its outer lateral edges on each side, upwardly from the holes 13, 13' at the approximate midpoint elevation of the patient's nose. The ends of the strap 2 pass through these holes, and are thereby attached to the plate member. The inner surface of the plate member 11 is provided with a layer of soft absorbent material 10' located in the upper portion of the plate resting on the bridge of the patient's nose. The strap 2 extends around the back of the patient's head, and serves as the primary support for the nose plate. The holes 14, 14' are sufficiently small in diameter to grip this strap frictionally, and this friction provides the means for attaching the strap 2 to the plate 11. The tension in the strap 2 is therefore adjusted by pulling the ends of the strap through these holes until the desired tension is reached. The tension in the stabilizing straps 3, 3' is similarly adjusted by sliding the ends of these straps along the main support strap 2. These ends are frictionally attached to the support strap 2 by slidable fittings on this strap. The stabilizing straps 3, 3' may be constructed from a single piece of elastic material by passing it through small holes 13, 13' directly above the tube-holding notch in the support plate. The elastic stabilizing strap is thereby frictionally gripped by these holes, and this arrangement further allows for a lateral adjustment of the attachment point of the support member along this strap.

This device may be quickly and easily slipped onto the patient's head, and the straps may be tightened by pulling on the ends. The absorbent material backing 10' insures that no discomfort to the patient's nose will arise while the device is in use. The support member 11 may be fabricated from a plastic transparent material, so that the nose and mouth of the patient remain visible while the device is in use. Access to the patient's nose and mouth may be obtained by lifting one edge of the device slightly without disturbing the endotracheal tube. Further, the tube may be quickly removed or reinserted into the supporting notch, without removing the device from the patient's head. This device is inexpensive and easily constructed, and may be sold as a disposable item. The tube holder may be emplaced in position on the patient after intubation of the endotracheal tube. It will be further seen that the endotracheal tube may be removed, replaced, or adjusted without removing, adjusting, or otherwise disturbing the tube holder. The position and stability of the emplaced tube holder are unaffected by movements of the patient's head, mouth, or jaw. The tube holder does not induce any trauma or injury to the mouth during emplacement or use. The use of elastic straps obviates the need for any adjustment other than simply tightening these straps, and allows rapid emplacement.

It will be appreciated that various modifications and changes may be made in the above-described endotracheal tube holder while preserving the features and advantages set forth, that the foregoing description and the drawing are illustrative and not limiting, and that the spirit and scope of the present invention are to be determined by reference to the appended claims.

What is claimed is:

1. An endotracheal tube holder, comprising:

a support member having an integral body adapted to fit over the oral-nasal region of the patient's face, said body having wall means adapted to be place over, and upwardly supported by, the nose of the patient said wall means having a lower peripheral edge spaced from the patient's face, and further having holding means formed in the lower portion of said peripheral edge adapted to firmly engage and hold in place an endotracheal tube in a substantially perpendicular direction to the oral cavity for delivery of vapors to and from the patient's lungs, said holding means being formed such that said tube may be introduced laterally into said holding means; and attachment means for attaching said support member to the patient's face, holding said support member firmly in place against the patient's nose and providing lateral support to said support member, including a main strap having opposite ends adapted to extend around the back of the patient's head, the two ends of said main strap being attached to either side of said support member, whereby said support member is maintained in place, and two supplemental straps having opposite ends, one end of each supplemental strap being attached to said support member at an elevational level different from the points of attachment of said main strap, the opposite ends of each supplemental strap being further connected to said main strap at positions on opposite sides of said support member, whereby said support member is provided further mechanical stability.

2. An endotracheal tube holder as recited in claim 1, wherein said wall means comprises a thin contoured plate shaped to fit over the patient's nose.

3. An endotracheal tube holder as recited in claim 2, wherein said thin contoured plate is constructed from transparent material.

4. An endotracheal tube holder as recited in claim 2, wherein said thin contoured plate is further provided with a thin layer of soft absorbent material attached to and lining the upper portion of its inner surface, such that said layer provides supporting contact with the patient's nose.

5. An endotracheal tube holder as recited in claim 2, wherein said holding means for holding in place the intubated endotracheal tube includes an indentation in the lower edge of said plate adjacent to the patient's mouth, said indentation being wider at its center than at a lower elevation, such that the endotracheal tube may be upwardly pressed in a direction perpendicular to the tubular axis into said indentation and is thereby firmly gripped by the edges of said indentation.

6. An endotracheal tube holder as recited in claim 1, wherein said main strap and said supplemental straps are constructed from elastic material.

7. An endotracheal tube holder as recited in claim 1, wherein said support member is provided with small constricting openings at the points of attachment of the ends of said main strap, and wherein said main strap is connected to said support member by passing its ends through said openings in said support member, said ends being squeezed and frictionally engaged by said openings, such that said main strap may be tightened and secured by pulling the ends through said openings.

8. An endotracheal tube holder as recited in claim 1, wherein said support member includes holes on either side at the points of attachment of said supplemental straps, and wherein said supplemental straps pass through said holes in said support member, being frictionally engaged by said holes, such that said straps are held in place by said holes and the points of attachment of said support member along said straps may be laterally adjusted.

9. An endotracheal tube holder comprising:

a support member having means adapted to be placed over, and upwardly supported by, the nose of the patient, and further having means adapted to firmly engage and hold in place an endotracheal tube in a substantially perpendicular direction to the oral cavity; and attachment means for attaching said support member to the patient's face, holding said support member firmly in place against the patient's nose and providing lateral support to said support member, including a main strap having opposite ends adapted to extend around the back of the patient's head, the two ends of said main strap being attached to either side of said support member, whereby said support member is maintained in place, and two supplemental straps having opposite ends, one end of each supplemental strap being attached to said support member at an elevational level different from the points of attachment of said main strap, the opposite ends of each supplemental strap being further connected to said main strap at positions on opposite sides of said support member, whereby said support member is provided further mechanical stability, wherein said supplemental straps are connected to said main strap by fittings slidably mounted on and frictionally constricting said main strap, such that said supplemental straps may be adjusted by sliding said fittings along said main strap.

* * * * *